United States Patent [19]
Burkovich et al.

[11] Patent Number: 5,456,883
[45] Date of Patent: Oct. 10, 1995

[54] MECHANISM FOR READING AND REMOVING REACTION CUVETTES IN AN INCUBATOR

[75] Inventors: Robert A. Burkovich; James D. Riall, both of Pittsford, N.Y.

[73] Assignee: Johnson & Johnson Clinical Diagnostics, Inc., Rochester, N.Y.

[21] Appl. No.: 266,070

[22] Filed: Jun. 27, 1994

[51] Int. Cl.⁶ .................................................. G01N 35/02
[52] U.S. Cl. ...................... 422/64; 422/63; 422/104; 435/809; 435/287.3; 436/43; 436/47; 436/48
[58] Field of Search ...................... 422/63, 64, 65, 422/52, 100, 103, 104; 436/43, 47, 48, 49, 807; 435/287, 312, 809

[56] References Cited

U.S. PATENT DOCUMENTS

| | | | |
|---|---|---|---|
| 4,406,547 | 9/1983 | Aihara | 356/414 |
| 4,476,733 | 10/1984 | Chlosta et al. | 73/863.91 |
| 4,595,562 | 6/1986 | Liston et al. | 422/65 |
| 4,699,766 | 10/1987 | Yamashita | 422/64 |
| 4,755,055 | 6/1988 | Johnson et al. | 356/440 |
| 5,093,268 | 3/1992 | Leventis et al. | 436/172 |
| 5,244,633 | 9/1993 | Jakubowicz et al. | 422/64 |

Primary Examiner—James C. Housel
Assistant Examiner—Long V. Le
Attorney, Agent, or Firm—Dana M. Schmidt

[57] ABSTRACT

An incubator comprises a rotor ring with two sets of apertures displaced along an arc of rotation, holding a cuvette in them. The apertures of one set are connected to an aperture of the other by a slot sized to allow passage of an elevator lead screw, but not a cuvette, between the apertures, the cuvette being raised on the top of the elevator during such passage. The elevator can also be used to move the cuvette into contact with a luminometer.

10 Claims, 5 Drawing Sheets

MECHANISM FOR READING AND REMOVING REACTION CUVETTES IN AN INCUBATOR

FIELD OF THE INVENTION

This invention relates to an incubator having an improved apparatus for moving a reaction cuvette into contact with a read station, and then out of the incubator.

BACKGROUND OF THE INVENTION

It is known to remove spent reaction cuvettes from an incubator for a "wet" analyzer, by transferring them from holding apertures in a rotor of the incubator, sideways until they occupy an adjacent aperture large enough to allow the cuvette to fall through to a dump basket. Such devices are shown, for example, in U.S. Pat. No. 4,406,547. However, in this arrangement, the dump aperture is connected to the holding aperture in such a way that a cuvette can inadvertently slide over, such as because of vibration or centrifugal force, and prematurely fall off the incubator. That is, the dump aperture is disposed radially outwardly from the holding aperture, immediately adjacent thereto.

It has, therefore, been a problem prior to this invention, that the dump aperture for the reaction cuvettes, while being conveniently located, nevertheless is disposed so that inadvertent dumping can occur.

Still further, prior wet analyzers have used read stations, for example, as in the aforesaid '547 patent, that do not position the reaction cuvette close to the detector since, for example, the cuvette cannot be readily moved toward the detector. Although this may be satisfactory for reflectometers or densitometers, it is not for luminometers that detect chemiluminescence, due to the greater sensitivity of luminometers. Chemiluminescence is preferred as it provides a gain in the read signal. In the latter case, the cuvette needs to be moved to a consistent position close to the detector, or vice-versa, for optimum performance, as is well-known.

Thus, prior to this invention, it has also been a problem to provide relative motion of a reaction cuvette and a chemiluminescent read station, without having yet another mechanism dedicated just to this function, since the more mechanisms that are present, the more unreliable the analyzer becomes.

SUMMARY OF THE INVENTION

We have designed an incubator that overcomes the aforementioned problems.

More specifically, in accord with one aspect of the invention, there is provided an incubator comprising a support for a reaction cuvette, the support having a first set of apertures therein sized for holding cuvettes against gravity, first means for moving the support about an axis, means for removing used cuvettes from the support, the removing means comprising a second set of apertures in the support adjacent the first set and a slot connecting each aperture of one set with an aperture of the other, each aperture of the second being sized larger than the cuvettes so that a cuvette in a second set aperture falls through the second set aperture if otherwise unsupported; the larger sized, second set of apertures being each displaced from the first set of apertures along an arc of rotation from the rotor;

and second means for moving a cuvette from an aperture of the first set to an aperture of the second set when the cuvette is ready for removal from the support.

In accord with another aspect of the invention, there is provided an incubator comprising a support for a reaction cuvette, the support having a first set of apertures therein sized for holding cuvettes against gravity, means for rotating the support about an axis, means for removing used cuvettes from the support, the removing means comprising a second set of apertures in the support adjacent the first set and a slot connecting each aperture of one set with an aperture of the other, each aperture of the second set being sized larger than the cuvettes so that a cuvette in a second set aperture falls through the second set aperture if otherwise unsupported, the slot being too narrow to allow sliding movement of a cuvette therealong from one of the first set of apertures to one of the second set, an elevator for raising a cuvette out of one of the first set of apertures, the elevator having an exterior dimension at a portion thereof that is less than the opening of the slot so as to allow the elevator to move relative to the first and second set of apertures through the slot, the elevator being operable from a first position below the apertures through and to a second position above the apertures, and a motor for raising and lowering the elevator to and from the first and second positions.

Accordingly, it is an advantageous feature of the invention that a spent reaction cuvette can be readily removed from the incubator without the risk of premature removal.

Another advantageous feature of the invention is that such a cuvette can be moved to a luminometer read station without a separate mechanism useful only for that purpose.

Other advantageous features will become apparent upon reference to the detailed Description of the Preferred Embodiments, when read in light of the attached drawings.

DESCRIPTION OF THE PREFERRED EMBODIMENTS

The following description concerns the preferred embodiments in which the incubator is utilized in an analyzer of a preferred construction, with preferred stations that interact with the incubator, and wherein a reaction cuvette is raised by an elevator for dumping, all by preferred mechanisms. In addition, the invention is useful regardless of the construction of the rest of the analyzer or its interacting stations, and regardless of the construction of the elevator.

Figure 1:
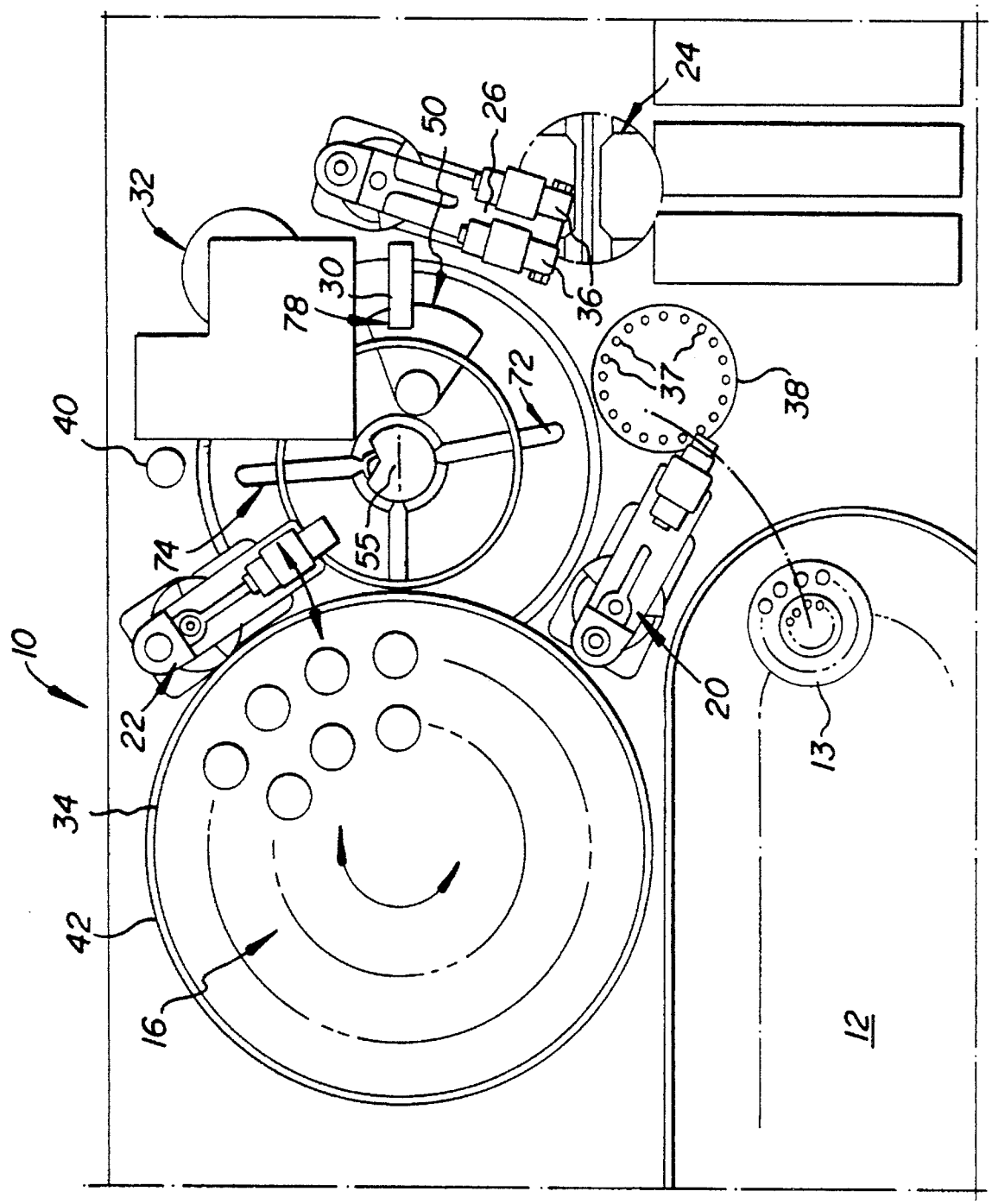
FIG. 1 is a fragmentary plan view of an analyzer in which the incubator of the invention is useful.
Figure 2:
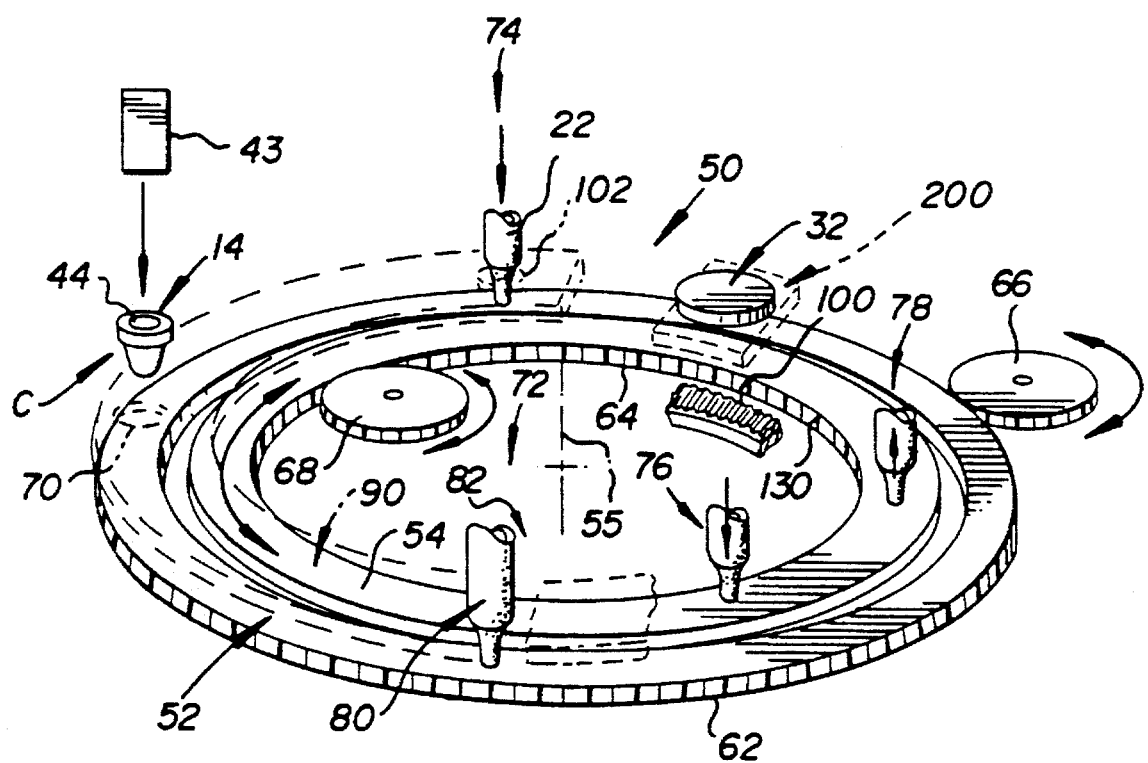
FIG. 2 is a partially schematic, isometric view of the two rotors of the incubator of the invention, showing the various stations.

As shown in FIG. 1, an analyzer 10 utilizing the incubator of the invention preferably comprises a sample supply station 12, a cuvette supply station 14, FIG. 2, a reagent supply station 16, FIG. 1, incubator 50, means 20 and 22 for transferring sample and reagent to a cuvette disposed in an outer ring of incubator 50, signal supply station 24, means 26 for transferring signal reagent to the cuvette in an inner ring of incubator 50, cuvette wash station 30, and luminometer 32, all as described in commonly-owned U.S. Pat. No. 5,244,633. Any suitable construction can be used for the sample supply station 12, cuvette supply station 14, reagent supply station 16, transfer means 20, 22 and 26, signal reagent supply station 24, wash dispenser 30, and luminometer 32. Useful sample transfer devices 13 include those described and claimed in commonly owned, U.S. application Ser. No. 859,780 filed on Mar. 30, 1992 by Tomasso et al, entitled "Tray and Magnetic Conveyor", now abandoned in favor of U.S. Continuation-in-Part application Ser. No. 036,800, filed Mar. 25, 1993, now U.S. Pat. No. 5,366,697. Supply station 16 includes rotor 34. Transfer means 20, 22 and 26 are all preferably pivoting aspirators, the aspirator at transfer means 26 having dual probes 36. Transfer means 20 preferably uses disposable tips, which can be presented for pick-up on supply station 12. Additional tips 37 can be presented on turntable 38 for use by means 20 during a dilution step. On the other hand, the aspirator for transfer means 22 preferably uses a more permanent dispensing tip, which uses a wash station 40 as is conventional.

Cuvettes can be disposed for dispensing at station 14 by mounting them in, e.g., a ring 42 that moves with rotor 16, any suitable pusher 43, FIG. 2, being used to displace a cuvette from ring 42 into incubator 50 below.

Although any cuvette can be used, preferably it is a cup-like container "C", having on its inside wall surface 44 an antibody pre-attached to the wall surface. The antibody is useful in a conventional sandwich assay which produces a complex of antibody-antigen-labeled antibody for generating a chemiluminescent signal.

Figure 3:
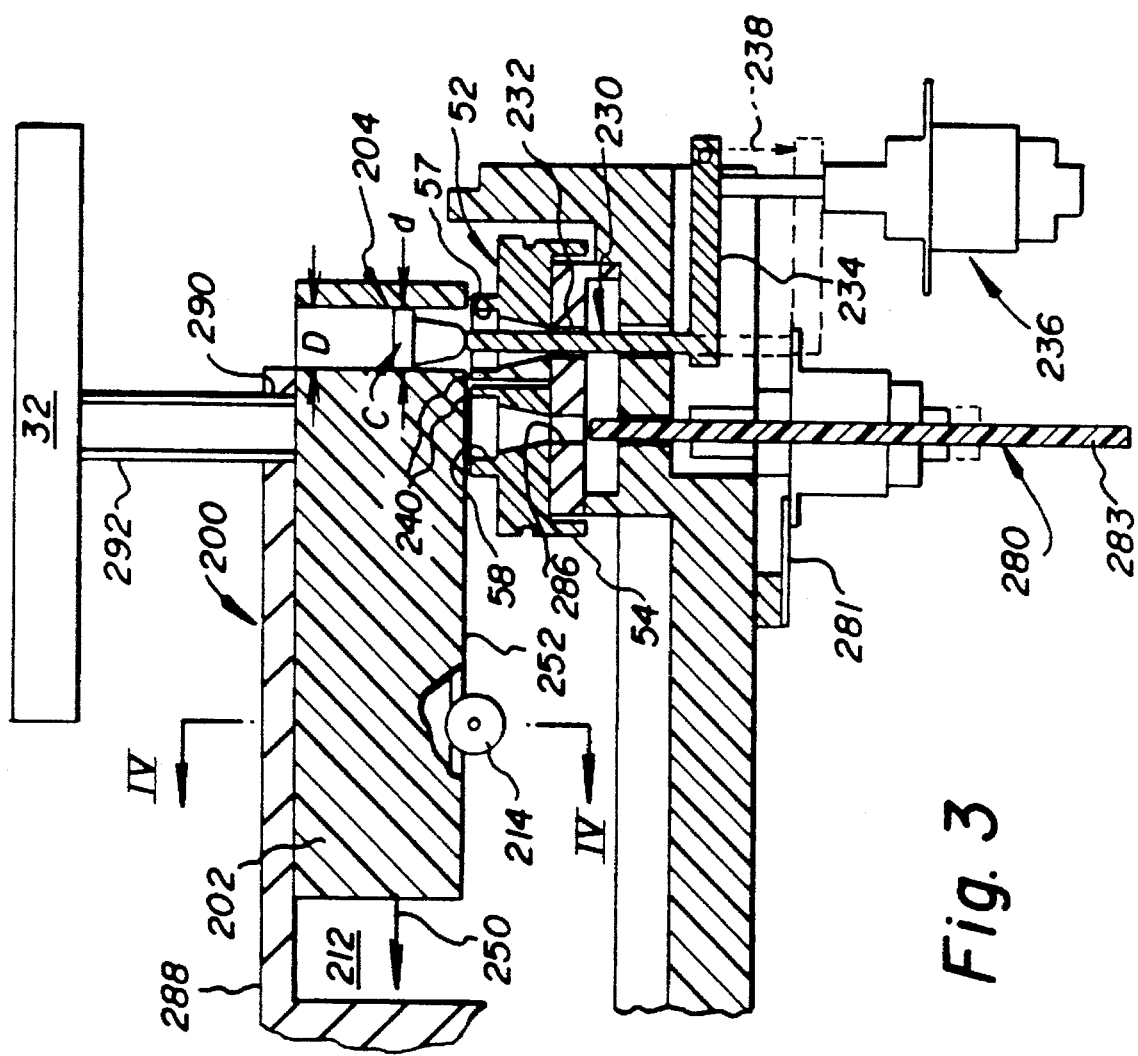
FIG. 3 is a fragmentary elevational view in section of the transfer mechanism and the elevator mechanism of the incubator.

The incubator is preferably that disclosed in said '633 patent, and comprises two rotors which are preferably two concentrically mounted support rings 52, 54 provided with holding apertures 57, 58, FIGS. 3 and 5, for receiving and carrying cuvettes C (delivered preferably first to ring 52 by any pusher means 43, FIG. 2), rotating means for independently rotating rings 52 and 54 about a common axis 55, transfer means 200 (FIG. 3) discussed hereinafter, for moving a cuvette from ring 52 to 54, processing stations round the rings, and heating means to incubate the contents of the cuvettes on rings 52 and 54. Rings 52 and 54 are shown only schematically in FIG. 2 in association with the related components. Rotating means for the rings preferably comprise gear teeth 62, 64 disposed on each of rings 52 and 54, respectively, to be driven by pinion gears 66 and 68.

As noted above, various processing stations are disposed around the circumference of rings 52 and 54, in addition to an entrance pork 70 for cuvettes C. They are as follows, FIGS. 1 and 2: Station 72 is permanently disposed above ring 52 and is the place to which the dispensing tip 37 of aspirator 20 (not shown in FIG. 2) pivots and descends to dispense sample into a cuvette in ring 52. First reagent addition station 74 is permanently disposed at least above ring 52 so that the permanent tip of aspirator 22 can dispense at least a first reagent into a cuvette in ring 52. Optionally, aspirator 22 can also be used to dispense a second reagent, namely a conjugate reagent, as well. Second reagent addition station 76, here for signal reagent, is disposed permanently above at least inner ring 54, to descend to dispense signal reagent into a cuvette in ring 54. Wash dispensing station 78 is disposed permanently above ring 54 for washing cuvettes using wash dispenser 30. Luminometer 32 is permanently disposed above ring 54 for reading chemiluminescence, using a mechanism discussed below. Finally, an elevator (FIGS. 3 and 5), discussed below, is disposed at station 280 to start the dumping of spent cuvettes from ring 54.

Transfer of cuvettes from ring 52 to ring 54 can be achieved by any suitable mechanism. Highly preferred is that mechanism 200 disclosed in U.S. Ser. No. 08/249,501 cofiled herewith, entitled "Transfer Mechanism Within an Incubator". In such a mechanism, FIGS. 3–5, a shuttle 202 is disposed above rotor rings 52 and 54, in between the rings and the luminometer 32. Shuttle 202 preferably has an aperture 204 or opening that is sufficiently large as to receive, without frictionally engaging, a cuvette C when such is lifted into the aperture. That is, the interior diameter "D" of aperture 204 is just larger than exterior diameter "d" of cuvette C that, without a support underneath a cuvette, a cuvette in the aperture will fall out of it.

Figure 4:
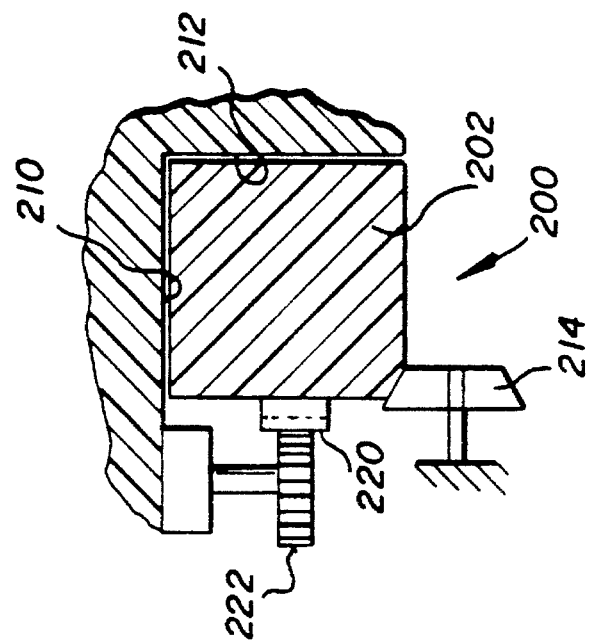
FIG. 4 is a sectional view taken generally along the line IV—IV of FIG. 3.
Figure 5:
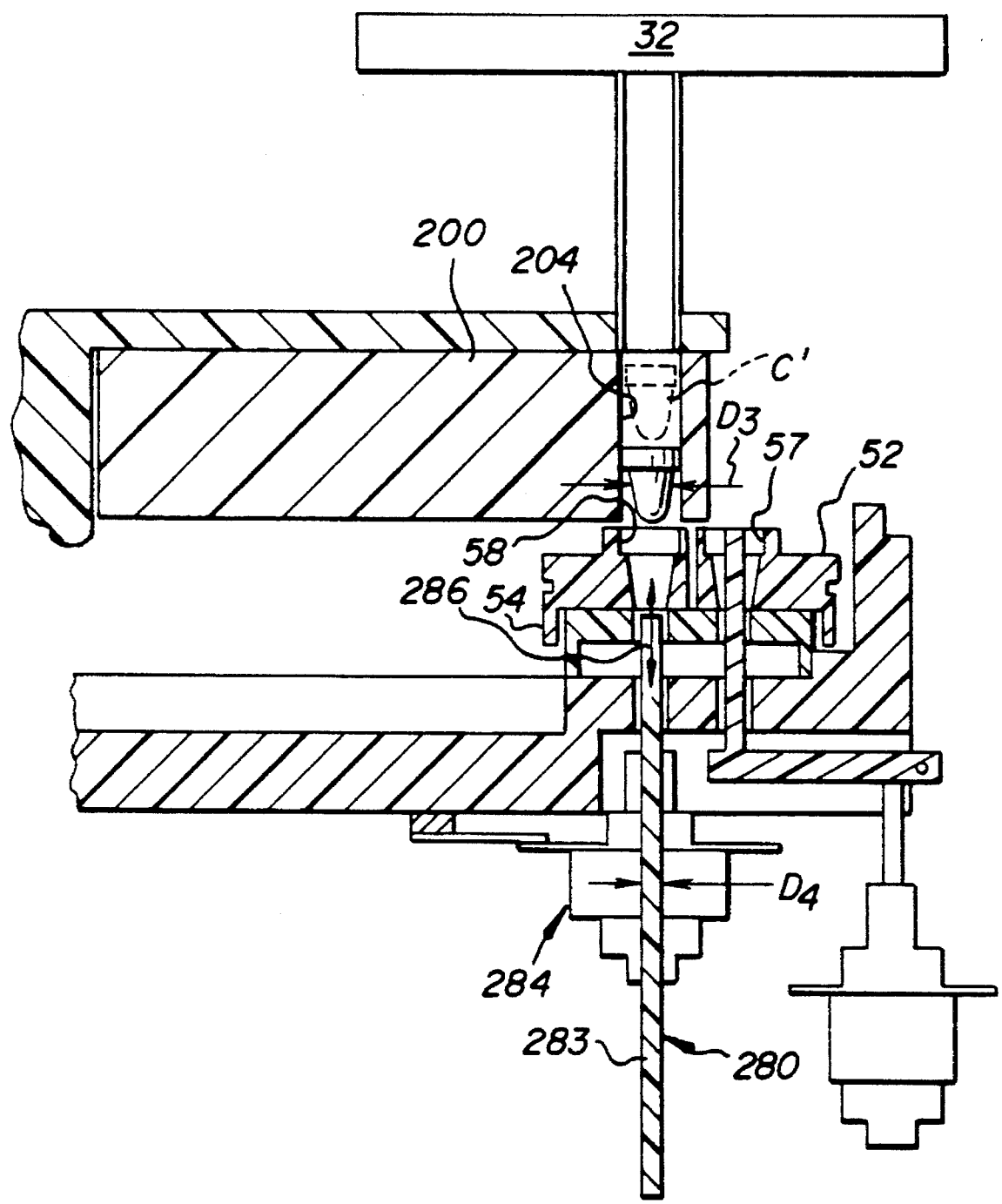
FIG. 5 is an elevational view similar to that of FIG. 3, showing the shuttle in its other position over the other rotor.

To allow shuttle 200 to move linearly from its position with aperture 204 aligned above ring aperture 57, to its position, FIG. 5, aligned above ring aperture 58, shuttle 200 is guided by any suitable means, such as guiding surface 210, 212 and guide roller 214, FIG. 4, that are part of the analyzer frame. To provide such movement relative to surfaces 210, 200 and roller 214, any suitable drive mechanism, such as a rack 220 and drive pinion 222, is useful.

To move a cuvette (preferably vertically) from its supported position in aperture 57 into aperture 204, a pusher member 230 is provided, mounted below ring 52. Specifically, an aperture 232 is provided in the frame below ring 52 to align with each of the apertures 57 as ring 52 passes thereabove. Member 230 is mounted within aperture 232, and is preferably integral with a lever arm 234 that is indexed up and down by a conventional motor, such as linear actuator motor 236. When member 230 and arm 234 are lowered, arrow 238, to the phantom position, member 230 is no longer within aperture 57 or in contact with a supported cuvette, but instead is below them.

Top surfaces 240 of rings 52 and 54 act as guide surfaces for cuvettes C as they are transferred over ring 52 to ring 54 by the movement of shuttle 200.

The method of transfer will be readily apparent from the preceding discussion. That is, a reaction cuvette C is raised out of ring 52 into shuttle 200 by first aligning aperture 204 above aperture 57, then raising member 230 to raise the cuvette into aperture 204. Shuttle 200 is then moved radially inwardly, arrow 250, FIG. 3, while the confined cuvette slides over guide surfaces 240. (Bottom edge 252 of shuttle 200 is designed to clear the top face of member 230.) As shown in FIG. 5, when aperture 204 is aligned with aperture 58, the transferred cuvette simply falls into place by gravity, into aperture 58, where it is supported and moved to stations for ring 54.

In accordance with the invention, reading and dumping of spent cuvettes is achieved by the following (FIGS. 3–6): A second elevator 280 is mounted on frame 281 of the analyzer, FIG. 3, in a first position below rotor ring 54. It preferably comprises a lead screw 283 driven by linear actuator motor 284. An opening 286 is provided above screw 283 to access apertures 58 in ring 54, in which a cuvette C can be positioned.

Frame 281 is preferably a compliant leaf spring, so that the cuvette can be pressed against its reference surface and the motor can overtravel a small amount.

Fixed immediately above shuttle 200 is a plate 288 having an aperture 290 in which an optical fiber 292 is inserted. This fiber extends a short distance to the luminometer 32, and is an operative part of the luminometer as an extension of its read optics. Aperture 290 and fiber 292 become aligned with aperture 204 when shuttle 200 is moved to its interior position, FIG. 5. At this point, elevator 280 is able, when sufficiently elevated, to push a cuvette C' (in phantom) into contact with fiber 292. This ensures that luminometer 32 will receive and read maximum light from any chemiluminescence reaction that occurs in cuvette C'.

Figure 6:
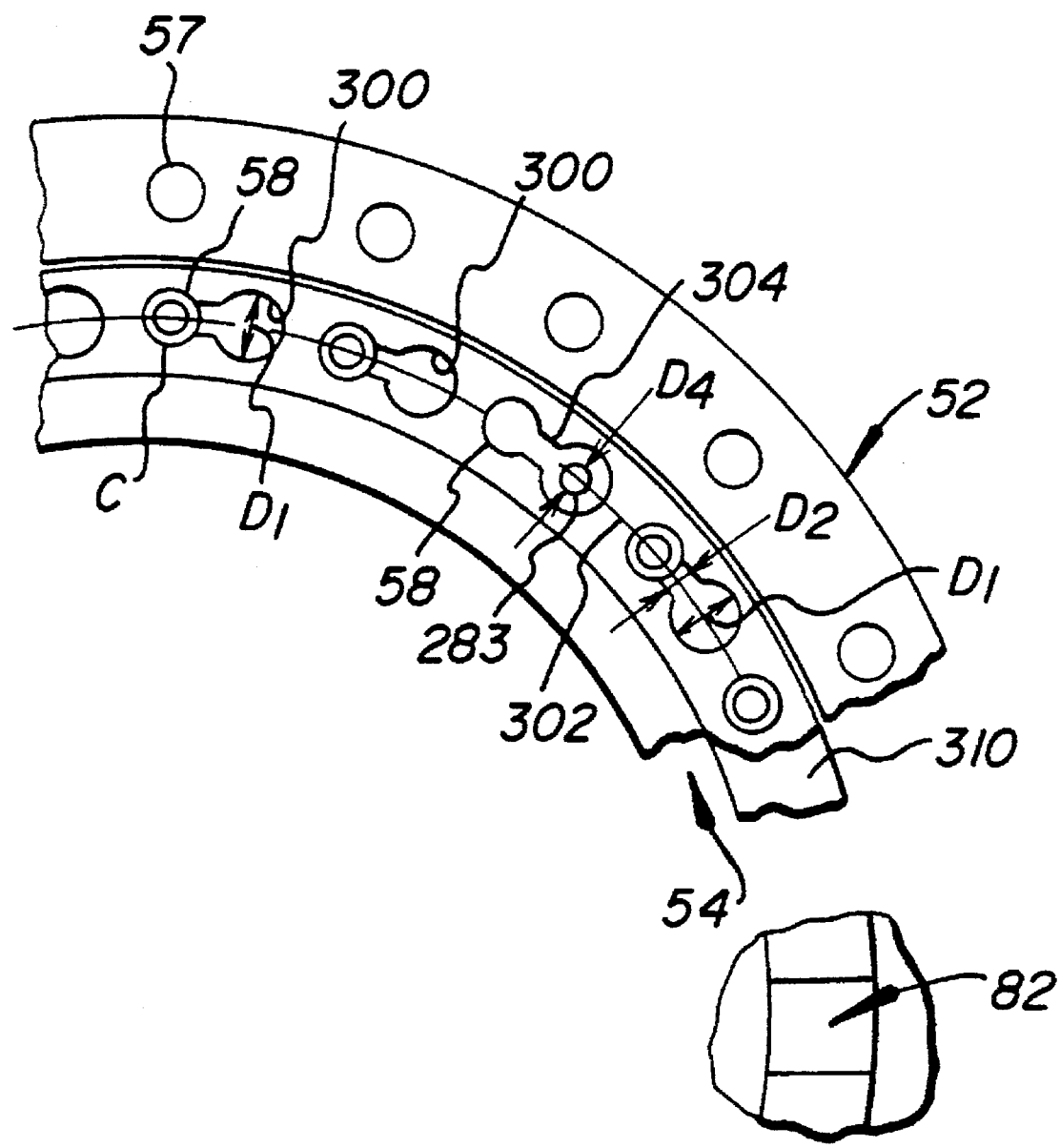
FIG. 6 is a fragmentary plan view of the rotor rings that illustrates the dumping apertures and slots.

To achieve the dumping of a cuvette C' after reading, ring 54 is modified to include an additional set of apertures 300, FIG. 6, each one of which is associated with apertures 58 spaced around the circumference of ring 54. That is, for each aperture 58 there is an additional aperture 300 displaced therefrom along an arc of rotation 302, and connected thereto via slot 304. The inside diameter $D_1$ of round apertures 300 is that much larger than the maximum diameter of cuvettes C and C' that, unless supported from below, such cuvettes will fall through apertures 300. To prevent that, there is a fixed support rail 310 other than at elevator 280 and dump station 82, over which ring 54 passes.

On the other hand, the maximum width $D_2$ of slot 304 is less than the diameter $D_3$, FIG. 5, of cuvettes C and C', so that they cannot slide into slot 304 and into aperture 300 inadvertently. However, the maximum outside diameter $D_4$ of screw 283, is less than $D_2$, so that rotor 54 can rotate while screw 283 projects through slot 304 to allow screw 283 to move, relative to ring 54, from an aperture 58 to an aperture 300, as shown. (The cuvette C' remains in aperture 204 during this maneuver.) Once this is achieved, screw 283 can be lowered to lower a cuvette C' into aperture 300, where it stays so long as rail 310 is in place under it.

However, rail 310 terminates at station 82 (also shown in FIG. 2) where there is a hole extending to a dump bin or basket which collects dumped cuvettes. That is, eventually ring 54 rotates aperture 300 holding a spent cuvette therein (not shown), until it aligns with the hole of station 82 and the cuvette drops through and out of the incubator.

By the aforesaid construction, the same elevator 280 is used to move cuvettes into contact with the luminometer, as is used to initiate the dump sequence of the read cuvettes, that is, as is used to transfer them to the enlarged apertures 300 that allow the cuvettes to fall away at station 82 where there is no longer an under-support rail 310.

Alternatively, however, it will be readily appreciated by one skilled that a separate elevator could be provided (not shown) to simply transfer a read cuvette C' from an aperture 58 to an aperture 300, some time after the cuvette C' has been lowered into aperture 300 by elevator 280.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. An incubator comprising a support for a reaction cuvette, said support having a first set of apertures therein sized for holding cuvettes against gravity, first means for moving the support about an axis, means for removing used cuvettes from the support, said removing means comprising a second set of apertures in said support adjacent said first set and a slot connecting each aperture of one set with an aperture of the other, each aperture of said second set being sized larger than the cuvettes so that a cuvette in a second set aperture falls through said second set aperture if otherwise unsupported; said larger sized, second set of apertures being each displaced from said first set of apertures along an arc of rotation of said support;

and second means for moving a cuvette from an aperture of said first set to an aperture of said second set when the cuvette is ready for removal from the support.

2. An incubator as defined in claim 1, and further including a dump elevator for raising a cuvette out of an aperture of said first set, said elevator being disposed under said support for projection up through said apertures and through said slot, so that a cuvette is raised up out of a first set aperture, said support is moved by said first moving means with the elevator passing through said slot, and said elevator and cuvette are lowered down through and into, respectively an aperture of said second set.

3. An incubator as defined in claims 1 or 2, and further including a stationary surface under said support, spaced to support a cuvette when in said second set of apertures, said stationary surface having at a location remote from said elevator, a dump hole through which a cuvette falls when moved thereto by said support.

4. An incubator as defined in claim 1 or 2, wherein said slot is sized to prevent a cuvette to slide over by itself from one of said first apertures to one of said second apertures.

5. An incubator as defined in claim 1 or 2, and further including a read station for reading light emitted from said cuvette, said read station being disposed above said support.

6. An incubator as defined in claim 5, and further including a read elevator for raising a cuvette out of an aperture of said first set into contact with said read station, said elevator being disposed under said support for projection up through said apertures and through said slot.

7. An incubator as defined in claim 6, wherein said read elevator and said dump elevator are the same elevator.

8. An incubator comprising a support for a reaction cuvette, said support having a first set of apertures therein sized for holding cuvettes against gravity, means for rotating the support about an axis, means for removing used cuvettes from the support, said removing means comprising a second set of apertures in said support adjacent said first set and a slot connecting each aperture of one set with an aperture of the other, each aperture of said second set being sized larger than the cuvettes so that a cuvette in a second set aperture falls through said second set aperture if otherwise unsupported, said slot being sized to prevent sliding movement of a cuvette therealong from one of said first set of apertures to one of said second set, and an elevator for raising a cuvette out of one of said first set of apertures, said elevator having an exterior dimension at a portion thereof that is less than the opening of said slot so as to allow said elevator to move relative to said first and second set of apertures through said slot, said elevator being operable from a first position below said apertures through and to a second position above said apertures, and a motor for raising and lowering said elevator to and from said positions.

9. An incubator as defined in claim 8, and further including a read station adjacent said second position so that said elevator is effective to raise a cuvette into position adjacent said read station when in said second position.

10. An incubator as defined in claim 9, wherein said read station is a luminometer.

* * * * *

UNITED STATES PATENT AND TRADEMARK OFFICE
CERTIFICATE OF CORRECTION

PATENT NO.   : 5,456,883
DATED        : Oct. 10, 1995
INVENTOR(S)  : Robert A. Burkovich, et al It is certified that error appears in the above-indentified patent and that said Letters Patent is hereby corrected as shown below:

```
       Column 6, line 29, replace
"in claim 1 or 2," with --in claim 2,-- therefor.
```

Signed and Sealed this

Thirtieth Day of January, 1996

Attest:

BRUCE LEHMAN

Attesting Officer

Commissioner of Patents and Trademarks